United States Patent [19]

Subramaniam et al.

[11] Patent Number: 5,594,156
[45] Date of Patent: Jan. 14, 1997

[54] SYNTHESIS OF SILYL CYANOHYDRINS

[75] Inventors: Chitoor S. Subramaniam, Kendall Park, N.J.; Gerald L. Larson, Newtown, Pa.

[73] Assignee: Huls America Inc., Somerset, N.J.

[21] Appl. No.: 516,644

[22] Filed: Aug. 18, 1995

[51] Int. Cl.$^6$ .................................. C07F 7/10; C07F 7/18
[52] U.S. Cl. ........................................ 556/417; 252/183.13
[58] Field of Search ...................... 556/417; 252/183.13

[56] References Cited

U.S. PATENT DOCUMENTS 3,658,868  4/1972  Muller et al. ............................ 556/417

OTHER PUBLICATIONS

K. Sukata, "A Convenient One–Pot Cyanosilylation of Aldehydes and Ketones Using Potassium or Sodium Cyanide Impregnated on Amberlite XAD Resin and Trimethylsilyl Chloride," vol. 60, No. 10, Bull. Chem. Soc. Jpn. (Oct. 1987), pp. 3820–3822.

"A Facile, One–Pot Synthesis of Silylated Cyanohydrins," Communications, Mar. 1978, pp. 219–222.

"A New Synthesis of β–Aminoalcohols via O–Silylated Cyanohydrins," Communications, Apr. 1981, pp. 270–272.

"A New, One–Pot Synthesis of Silylated Cyanohydrins," Communications, Mar. 1982, pp. 212–214.

"A New Synthesis of 1–Aminoalcohols from O–Trimethylsilylated Cyanohydrins," Communications, Mar. 1986, pp. 301–303.

*Primary Examiner*—Paul F. Shaver
*Attorney, Agent, or Firm*—Abelman, Frayne & Schwab

[57] ABSTRACT

A process for preparing silyl cyanohydrins that comprises reacting an aldehyde or ketone with a hydrogen cyanide, a trisubstituted halosilane and a correspondingly substituted disilazane or silyl amine.

11 Claims, No Drawings

SYNTHESIS OF SILYL CYANOHYDRINS

FIELD OF THE INVENTION

The present invention relates to a method for synthesizing silyl cyanohydrins.

BACKGROUND OF THE INVENTION

O-protected cyanohydrins, such as O-trimethylsilyl cyanohydrins, have considerable utility as precursors to biologically important compounds and are useful as acyl anion equivalents in many synthetic transformations.

Several one-pot methods for synthesizing silylated cyanohydrins are known. Rasmussen and Heilmann (Synthesis, Mar. 1978, pp. 219–21) disclose refluxing a carbonyl compound (aldehydes or ketones) with solid potassium cyanide and chlorotrimethylsilane in either acetonitrile or dimethylformamide solvent. Sukata (Bull. Chem. Soc. Jpn., v.60 n.10, 1987, pp. 3820–22) discloses reacting an aldehyde or a ketone with methylsilylchloride in the presence of a solvent and Amberlite XAD resin that has been impregnated with potassium cyanide or sodium cyanide. Duboudin and co-workers (Synthesis, Mar. 1982, pp. 212–14) disclose mixing chlorotrimethylsilane and potassium cyanide in acetonitrile and in the presence of a catalytic amount of sodium iodide and pyridine. These methods require expensive reagents, cyanide salts, solvents and catalyst adding to the complexity and cost of the cyanosilylation reaction.

SUMMARY OF THE INVENTION

An object of the present invention is to provide a direct one-pot synthesis of silylated cyanohydrins.

A second object of the present invention is to provide a method for producing trimethylsilyl cyanohydrin that avoids isolating trimethylsilyl nitrile.

A third object of the present invention is to provide a method for producing silylated cyanohydrins that avoids using expensive reagents, cyanide salts and solvents.

These and other objects are met by a process for preparing silyl cyanohydrins that comprises reacting an aldehyde or ketone with a hydrogen cyanide, tri-substituted halosilane and a corresponding substituted disilazane or silyl amine.

DETAILED DESCRIPTION OF THE INVENTION

In a method according to the present invention, a carbonyl compound such as an aldehyde or a ketone can be cyanosilylated to form a silyl cyanohydrin. According to one such method, the aldehyde or ketone is reacted with tri-substituted halosilane, hydrogen cyanide and disilazane or silyl amine to form a silyl cyanohydrin. The disilazane and silyl amine are substituted with the same species as the halosilane. The aforementioned reactions can be represented as follows:

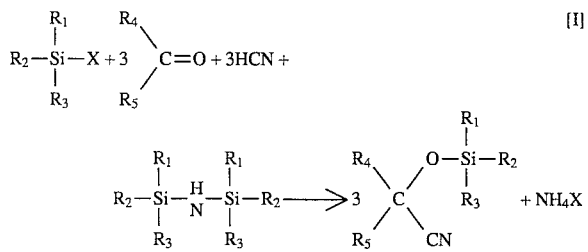

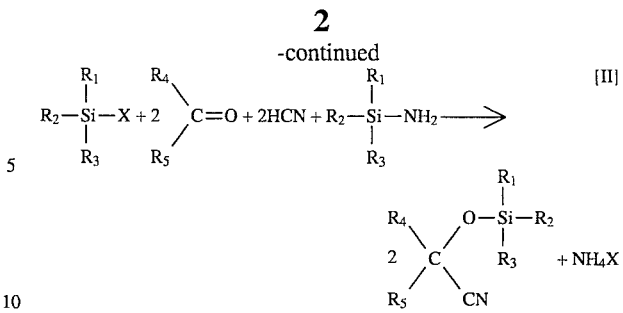

The reagents, following either equation I or II, are preferably reacted in about stoichiometric amounts. Thus, according to equation I, the preferred molar ratios are as follows: carbonyl compound to tri-substituted halosilane to hydrogen cyanide to substituted disilazane is about 3:1:3:1. According to equation II, the preferred molar ratios are as follows: carbonyl compound to tri-substituted halosilane to hydrogen cyanide to substituted silyl amine is about 2:1:2:1. Stoichiometric amounts of reactants are preferred to minimize difficulties related to product purification and safety. A slight excess of the tri-substituted halosilane up to about 5 percent by weight is tolerable but excess hydrogen cyanide should be avoided.

The substituents $R_1$, $R_2$ and $R_3$ can be as follows, in accordance with the invention:

(a) $R_1=R_2=R_3$ is an aryl or $C_1$ to $C_6$ alkyl group; or (b) $R_1$ is t-butyl and $R_2=R_3$ is an aryl or $C_1$ to $C_6$ alkyl group; or (c) $R_1$ is an aryl group and $R_2=R_3$ is a $C_1$ to $C_6$ alkyl group.

For each combination, (a)–(c), of substituents, $R_1$–$R_3$, X can be Cl, Br or I. Further, for each combination, the $C_1$ to $C_6$ alkyl group can be a branched, unbranched, saturated, unsaturated, substituted or unsubstituted, cyclic or acyclic group, including the isopropyl, isobutyl, sec-butyl, tert-butyl, neopentyl, n-hexyl and the like groups. The aryl group includes the phenyl, benzyl, naphthyl, phenanthranyl, anthranyl and the like groups and generally can include up to three rings. Further, such aryl groups can have one or more substituents including halo, alkyl, aralkyl, aryl, alkoxy, cyano, ether and the like groups.

Regarding the carbonyl compound, $R_4$ and $R_5$ can each be hydrogen or a $C_1$ to $C_{30}$ group. The carbon group(s) can be a branched, unbranched, saturated, unsaturated, substituted or unsubstituted, cyclic or acyclic, aryl or alkyl group.

When $R_4$ is hydrogen and $R_5$ is hydrogen or $C_1$ to $C_{30}$, then the carbonyl group is an aldehyde. Examples of suitable aldehydes include, without limitation, formaldehyde, acetaldehyde, benzaldehyde and steroidal aldehydes. When $R_4$ is a methyl group and $R_5$ is $C_1$ to $C_{30}$, then the carbonyl group is a ketone. Examples of suitable ketones include, without limitation, acetone, cyclohexanone, acetophenone and steroidal ketones.

According to a preferred embodiment of the present invention, the carbonyl compound, tri-substituted halosilane and hydrogen cyanide are combined. The corresponding disilazane or silyl amine is then added dropwise to the aforementioned combination of reactants. The reaction is exothermic so that the temperature of the reaction mixture increases. The addition of disilazane or silyl amine is controlled so that the temperature of the reaction mixture increases from ambient to about 90° to 100° C.

Ammonium halide is formed as a by-product in the method according to the present invention. The reaction mixture is preferably cooled to about 10° C. before removal of the ammonium halide by filtration. Preferably, the ammonium halide filtrate is washed with ether or other suitable solvents such as hexane, tetrahydrofuran or toluene, for example. The organic wash and the organic phase are combined and distilled under reduced pressure to yield the silylated cyanohydrin product.

In a preferred embodiment of the present invention, the trisubstituted halosilane is trimethylchorosilane and hexamethyldisilazane, rather than silyl amine, is used.

Table 1 below lists a few of the many silyl cyanohydrins that can be synthesized according to the present method:

TABLE 1

| Ex. | Carbonyl Compound | Chloro-Silane | Disilazane/ Silyl Amine | Silyl Cyanohydrin |
|---|---|---|---|---|
| 1 | benzaldehyde | trimethyl | hexamethyldisilazane | Benzene Acetonitrile-α-[(trimethylsilyl)oxy] |
| 2 | cyclohexanone | trimethyl | hexamethyldisilazane | Cyclohexane Carbonitrile-1-[(trimethylsilyl)oxy] |
| 3 | 2-ethylbutyraldehyde | trimethyl | hexamethyldisilazane | Propane Carbonitrile-1-ethyl-1[(trimethylsilyl)oxy] |
| 4 | 3-pentanone | trimethyl | hexamethyldisilazane | Butane Carbonitrile-2-ethyl-1[(trimethylsilyl)oxy] |
| 5 | benzaldehyde | phenyldimethyl | 1,3 diphenyl tetramethyl disilazane | Benzene Acetonitrile-α-[(phenyldimethylsilyl)oxy] |
| 6 | cyclohexanone | t-butyldimethyl | t-butyldimethyl silyl amine | Cyclohexane Carbonitrile-1-[(t-butyldimethylsilyl)oxy] |
| 7 | 2-ethylbutyraldehyde | t-butyldiphenyl | t-butyldiphenyl silyl amine | Propane Carbonitrile-1-ethyl-1[(t-butyldiphenylsilyl)oxy] |
| 8 | 3-pentanone | tri-n-hexyl | tri-n-hexyl silyl amine | Butane Carbonitrile-2-ethyl-1[(tri-n-hexylsilyl)oxy] |

Further details of the synthesis of the silyl cyanohydrins of Examples 1–4 are provided below. It should be understood that one of ordinary skill in the art will be able to synthesize other silyl cyanohydrins within the scope of this invention, including those of Examples 5–8, above, based on the present teachings.

EXAMPLE 1

Synthesis of benzene acetonitrile-α[(trimethylsilyl)oxy]

150 grams (g) (1.4 mols) of benzaldehyde, 60 g (0.55 mols) of trimethylchlorosilane and 40 g (1.48 mols) of hydrogen cyanide were added to a 500 ml, four-necked flask equipped with an overhead stirrer, thermometer, addition funnel and water-cooled condenser. 100 g (0.62 mols) of hexamethyldisilazane were added dropwise to the flask over the course of about 3 hours. Ammonium chloride by-product was washed twice with ether. The ether wash and the organic phase were combined and distilled at 0.5 mm Hg. Yield of the product benzene acetonitrile-α[(trimethylsilyl)oxy] was 82 percent. The product was characterized as follows- bp: 91° C. at 0.5 mm; IR: $\upsilon_{max}$=2243 cm$^{-1}$ (CN); $^1$H NMR δppm (CDCl$_3$) 0.2 (s,9H), 5.5 (s,1H) and 7.3–7.5 (m, 5H); $^{13}$C NMR δppm (CDCl$_3$) 0.4, 64, 119, 126.8, 129.3, 129.1 and 137.

EXAMPLE 2

Synthesis of cyclohexane carbonitrile-1-(trimethylsilyl)oxy 158 g (1.6 mols) of cyclohexanone, 60 g (0.55 mols) of trimethylchlorosilane and 45 g (1.66 mols) of hydrogen cyanide were added to a flask as described in Example 1. 100 g (0.62 mols) of hexamethyldisilazane were added as described in Example 1. After ether wash and distillation under vacuum at 35 mm Hg, a 77 percent yield of cyclohexane carbonitrile-1 -(trimethylsilyl)oxy product was obtained. The product was characterized as follows—bp: 115° C. at 35 mm; IR: $\upsilon_{max}$=2239 cm$^{-1}$ (CN); $^1$H NMR δppm (CCl$_4$) 0.1 (s,9H) and 1.2–1.9 (m,10H); $^{13}$C NMR δppm (CCl$_4$) 2.0, 23.2, 25.2, 40.0, 70.0 and 121.

EXAMPLE 3

Synthesis of Propane Carbonitrile-1-ethyl-1(trimethylsilyl)oxy

Following the procedure outlined in Examples 1 and 2, 25 g (0.25 mols) of 2-ethylbutyraldehyde, 8.9 g (0.08 tools) of trimethylchlorosilane, 6.8 g (0.25 mols) of hydrogen cyanide and 13.3 g (0.08 mols) of hexamethyldisilazane were reacted yielding 91 percent of the product (GC assay). The product was characterized as follows—$^1$H NMR δppm (CCl$_4$) 0.1 (s, 9H) and 0.8 (t,6H), 1.4 (m,4H) and 4.3 (d,1H); $^{13}$C NMR δppm (CCl$_4$) 0.9, 10.7, 10.8, 21.1, 21.2, 46.1, 63.4 and 118.2.

EXAMPLE 4

Synthesis of Butane Carbonitrile-2-ethyl-1(trimethylsilyl)oxy

Following the procedure outlined in Examples 1 and 2, 21.5 g (0.25 mols) of 3-pentanone, 8.9 g (0.08 mols) of trimethylchlorosilane, 6.8 g (0.25 mols) of hydrogen cyanide and 13.3 g (0.08 mols) of hexamethyldisilazane were reacted yielding 95 percent of the product (GC assay). The product was characterized as follows—$^1$H NMR δppm (CCl$_4$) 0.1 (s,9H) and 0.9 (t,6H), 1.6 (q,4H); $^{13}$C NMR δppm (CCl$_4$) 0.67, 7.1, 33, 73.5 and 120.

We claim:

1. A method for forming a silylated cyanohydrin comprising the steps of:

a) combining a carbonyl compound selected from the group consisting of aldehydes and ketones with hydrogen cyanide and a trisubstituted halosilane selected from the group consisting chlorosilane, bromosilane and iodosilane; and b) forming a reaction mixture by adding a reactant selected from the group consisting of disilazane and silyl amine to the combination of step (a).

2. The method of claim 1 wherein the reactant of step b) is disilazane and the molar ratio of the carbonyl compound to trisubstituted halosilane to hydrogen cyanide to disilazane is about 3:1:3:1.

3. The method of claim 1 wherein the reactant of step b) is silyl amine and the molar ratio of the carbonyl compound to trisubstituted halosilane to hydrogen cyanide to silyl amine is about 2:1:2:1.

4. The method of claim 1 wherein the trisubstituted halosilane is a trisubstituted chlorosilane that is selected from the group consisting of trimethyl chlorosilane, phenyldimethylchlorosilane, t-butyldimethylchlorosilane, t-butyldiphenylchlorosilane and tri-n-hexylchlorosilane.

5. The method of claim 1 wherein the trisubstituted halosilane is trimethylchlorosilane and the disilazane is hexamethyldisilazane and the silylated cyanohydrin is trimethylsilyl cyanohydrin.

6. The method of claim 1 wherein the combination of step (a) is at ambient temperature.

7. The method of claim 1 wherein the reactant is added in a manner such that the temperature of the reaction mixture does not exceed about 100° C.

8. A method for forming a silyl cyanohydrin comprising the steps of:
   a) combining a carbonyl compound selected from the group consisting of aldehydes and ketones with hydrogen cyanide and $(R_1)(R_2)(R_3)Si-X$ and
   b) forming a reaction mixture by adding, to the combination of step a), a reactant selected from the group consisting of:
   $(R_1)(R_2)(R_3)Si-NH-Si(R_1)(R_2)(R_3)$ and
   $(R_1)(R_2)(R_3)Si-NH_2$,
   wherein:
      X is a halogen selected from the group consisting of Cl, Br and I; and, either
      $R_1$, $R_2$ and $R_3$ are the same aryl or $C_1$ to $C_6$ alkyl group, or
      $R_1$ is t-butyl and $R_2$ and $R_3$ are the same aryl or $C_1$ to $C_6$ alkyl group, or
      $R_1$ is an aryl group and $R_2$ and $R_3$ are the same $C_1$ to $C_6$ alkyl group,
   and further wherein:
      when the reactant is $(R_1)(R_2)(R_3)Si-NH-Si(R_1)(R_2)(R_3)$, the molar ratio of the carbonyl compound to $(R_1)(R_2)(R_3)Si-X$ to hydrogen cyanide to $(R_1)(R_2)(R_3)Si-NH-Si(R_1)(R_2)(R_3)$ is about 3:1:3:1, and
      when the reactant is $(R_1)(R_2)(R_3)Si-NH_2$, the molar ratio of the carbonyl compound to $(R_1)(R_2)(R_3)Si-X$ to hydrogen cyanide to $(R_1)(R_2)(R_3)Si-NH_2$ is about 2:1:2:1.

9. The method of claim 8 wherein the reactant is $(R_1)(R_2)(R_3)Si-NH-Si(R_1)(R_2)(R_3)$ and $R_1$, $R_2$ and $R_3$ are methyl groups.

10. A reaction mixture for preparing a silyl cyanohydrin comprising a carbonyl compound selected from the group consisting of aldehydes and ketones, a trisubstituted halosilane, hydrogen cyanide and a reactant selected from the group consisting of a substituted disilazane and a substituted silyl amine, wherein the disilazane and silyl amine are substituted with the same species as the halosilane.

11. The reaction mixture of claim 10 wherein the trisubstitued halosilane is trimethylchlorosilane and the substitued disilazane is hexamethyldisilazane.

* * * * *